US008143565B2

(12) United States Patent
Berkner et al.

(10) Patent No.: US 8,143,565 B2
(45) Date of Patent: Mar. 27, 2012

(54) ADJUSTABLE MULTIMODE LIGHTFIELD IMAGING SYSTEM HAVING AN ACTUATOR FOR CHANGING POSITION OF A NON-HOMOGENEOUS FILTER MODULE RELATIVE TO AN IMAGE-FORMING OPTICAL MODULE

(75) Inventors: Kathrin Berkner, Los Altos, CA (US); M. Dirk Robinson, Menlo Park, CA (US); Jun Ke, Tucson, AZ (US)

(73) Assignee: Ricoh Co., Ltd., Tokyo (JP)

( * ) Notice: Subject to any disclaimer, the term of this patent is extended or adjusted under 35 U.S.C. 154(b) by 353 days.

(21) Appl. No.: 12/571,010

(22) Filed: Sep. 30, 2009

(65) Prior Publication Data
US 2011/0073752 A1    Mar. 31, 2011

(51) Int. Cl.
*H01L 27/00* (2006.01)
(52) U.S. Cl. ................. 250/208.1; 250/226
(58) Field of Classification Search ............... 250/208.1, 250/226, 216; 355/53, 55, 67–71; 356/39, 356/435–443; 359/351–357, 364, 857
See application file for complete search history.

(56) References Cited

U.S. PATENT DOCUMENTS

| 6,927,836 B2* | 8/2005 | Nishinaga ............... 355/53 |
| 7,433,042 B1 | 10/2008 | Cavanaugh et al. |
| 2008/0204744 A1 | 8/2008 | Mir et al. |
| 2009/0096914 A1 | 4/2009 | Domenicali |

OTHER PUBLICATIONS

Cavanaugh, D.B. et al., "VNIR Hypersensor Camera System," Proc. SPIE, conference Aug. 3, 2009, online publication Aug. 17, 2009, 17 pages, vol. 7457.
Choi, J. et al., "Zoom Lens Design for a Novel Imaging Spectrometer That Controls Spatial and Spectral Resolution Individually," Applied Optics, 2006, pp. 3430-3441, vol. 45.
Elliott, K.H., "A Novel Zoom-Lens Spectrograph for a Small Astronomical Telescope," Mon. Not. R. Astron. Soc., 1996, pp. 158-162, vol. 281.
Fife, K. et al., "A 3D Multi-Aperture Image Sensor Architecture," Proc. of IEEE Custom Integrated Circuits Conference, 2006, pp. 281-284.
Gehm, M. et al., "Single-Shot Compressive Spectral Imaging with a Dual-Disperser Architecture," Optics Express, Oct. 17, 2007, pp. 14013-14027, vol. 15, No. 21.
Harvey, A.R. et al., "Spectral Imaging in a Snapshot," Proc. of SPIE, 2005, pp. 110-119, vol. 5694.
Harvey, A.R. et al., "Technology Options for Hyperspectral Imaging," Proc. of SPIE, 2000, pp. 13-24, vol. 4132.
Horstmeyer, R. et al., "Flexible Multimodal Camera Using a Light Field Architecture," IEEE Conf. on Computational Photography, 2009, pp. 1-8.
Shogenji, R. et al., "Multispectral Imaging Using Compound Optics," Optics Express, Apr. 19, 2004, pp. 1643-1655, vol. 12, No. 8.

* cited by examiner

*Primary Examiner* — Que T Le
(74) *Attorney, Agent, or Firm* — Fenwick & West LLP

(57) ABSTRACT

An adjustable multimode lightfield imaging system. A non-homogeneous filter module is positioned at the aperture plane of the lightfield imaging system and provides the multimode capability. The filter module can be moved relative to the imaging system, thus allowing adjustment of the multimode capability.

20 Claims, 7 Drawing Sheets

ADJUSTABLE MULTIMODE LIGHTFIELD IMAGING SYSTEM HAVING AN ACTUATOR FOR CHANGING POSITION OF A NON-HOMOGENEOUS FILTER MODULE RELATIVE TO AN IMAGE-FORMING OPTICAL MODULE

BACKGROUND OF THE INVENTION

1. Field of the Invention

This invention relates generally to multimode imaging systems using filter modules, and, more particularly, to such systems where the multimode characteristics can be changed by a relative motion of the filter module.

2. Description of the Related Art

A multimode imaging system is an imaging system that can capture information beyond the usual spatial information acquired by conventional imaging systems (e.g., those based on RGB Bayer patterns). For example, a multimode imaging system might acquire additional spectral information (multispectral and hyperspectral systems) to be used for spectral analysis or identification of substances. Multimode imaging systems might also capture information about the polarization of a scene, or even provide a higher dynamic range than that provided by the inherent capability of the detector array.

Acquiring this additional information can be difficult since most commercially available detector arrays spatially segment the incoming image into a two-dimensional image signal. Traditionally, the additional information of spectra, polarization or other modes was acquired by time multiplexing. For example, in spectral imaging applications, it might be desirable to acquire radiation from an object at different wavelengths of interest. The number of wavelength bands of interest may be between 5 and 20 for multispectral imagers and more than 20 for hyperspectral imagers. Traditional multispectral or hyperspectral imagers are based either on a filter wheel that contains wavelength filters that correspond to the wavelength bands of interest or on dispersive elements such as prisms or gratings. In case a filter wheel is used, at any one time, only one of the wavelength filters is positioned in the imaging path. The filter wheel rotates in order to switch from one wavelength filter to the next. Thus, the multispectral or hyperspectral imaging is implemented in a time multiplexed manner. However, the resulting systems can be large and complicated. In case dispersive elements are used to spatially separate different wavelengths, the light is typically dispersed along one dimension of the detector array. The other dimension is used to capture one spatial dimension of the object. However, it is difficult to also capture the second spatial dimension of the object. Sometimes, time multiplexing is introduced to capture the second spatial dimension, for example by scanning.

Recently, there has been an increased attention on acquiring multimode information of a scene simultaneously, or in a "single snapshot." These single-snapshot systems multiplex the different mode signals onto different detector pixels in the detector array. That is, the multimode information is spatially multiplexed rather than time multiplexed.

Single snapshot multispectral imaging architectures can generally be categorized into two classes. One class uses dispersive elements, such as prisms or gratings, to spatially separate different wavelengths in combination with some beam splitting element, e.g. a prism or a mask. This architecture has the disadvantage that the dispersive element is typically applied to either a collimated beam or at an intermediate image plane. As a result, many of these systems are 4-f systems (four times the effective focal length of the optical system), which results in an optical system that is quite large and has limited field of view.

In the other class of single snapshot imagers, separate filters are attached to each detector in a manner similar to the RGB Bayer pattern found in conventional color imaging systems. That is, a color filter array is laid out on top of the detector array, so that individual filters (which will be referred to as micro-filters) each filter the light directed to individual detectors. The individual micro-filters are designed to implement the multimode imaging. For example, the filter array might include micro-filters with 20 different wavelength responses in order to implement multispectral imaging. One disadvantage of this class of systems is the increased cost and complexity of manufacturing. Because there is a one-to-one correspondence between micro-filters and detectors, and because the micro-filters are attached to the detectors, the micro-filters are the same size as the detectors, which is small. The many different small micro-filters must then be arranged into an array and aligned with the underlying detectors. Another disadvantage is the lack of flexibility. Once the micro-filter array is attached to the detector array, it is difficult to change the micro-filter array.

Thus, there is a need for improved multimode imaging systems.

SUMMARY OF THE INVENTION

The present invention overcomes the limitations of the prior art by providing an adjustable multimode lightfield imaging system. A non-homogeneous filter module is positioned at or near the aperture plane of the lightfield imaging system and provides the multimode capability. The filter module can be moved relative to the imaging system, thus allowing adjustment of the multimode capability.

In one embodiment, an adjustable multimode lightfield imaging system includes an image-forming optical module, a non-homogeneous filter module, an array of micro-imaging elements, a detector array and an actuator. The optical module forms an optical image of an object. The non-homogeneous filter module is positioned at the aperture plane. By moving the filter module relative to the optical module, different portions of the filter module are illuminated by the object. The array of micro-imaging elements is positioned at the image plane, and the detector array is positioned in a conjugate plane to the aperture plane. The micro-imaging elements image the illuminated portion of the filter module onto the detector array. The detectors receive light collected by the micro-imaging elements, as filtered by corresponding locations of the filter module. The actuator moves the filter module relative to the optical module, thus changing the multimode filtering.

In one class of systems, the non-homogeneous filter module is a filter array where the filters are not all the same. The different types of filters capture the multimode information. For example, the filters may include one or more different wavelength filters, polarization filters, luminance filters and/or neutral density filters. In some applications, the filter array is designed to implement multispectral or hyperspectral imaging, or to detect different substances.

Other aspects of the invention include methods corresponding to the devices and systems described above, and applications for the foregoing.

BRIEF DESCRIPTION OF THE DRAWINGS

The invention has other advantages and features which will be more readily apparent from the following detailed description of the invention and the appended claims, when taken in conjunction with the accompanying drawings, in which:

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION OF THE PREFERRED EMBODIMENTS

Figure 1A:
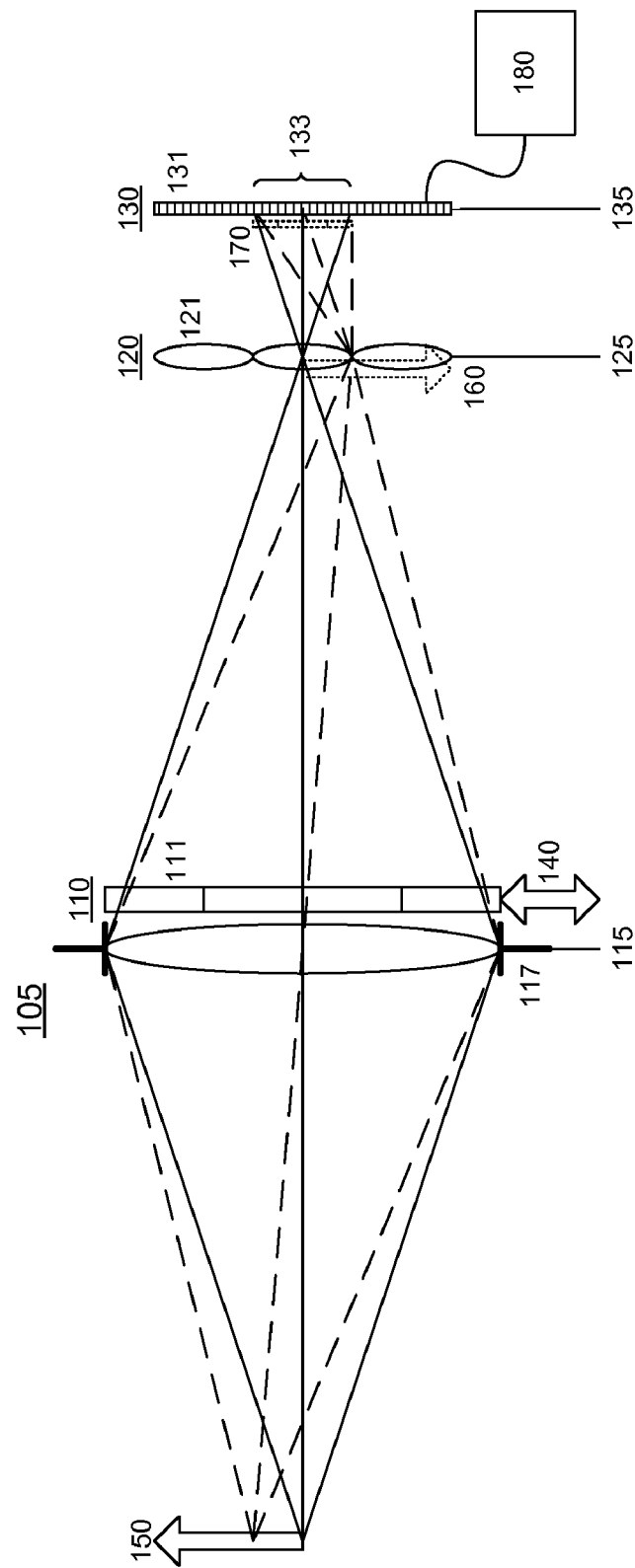
FIG. 1A is a diagram of an adjustable multimode lightfield imaging system according to the invention.
Figure 1B:
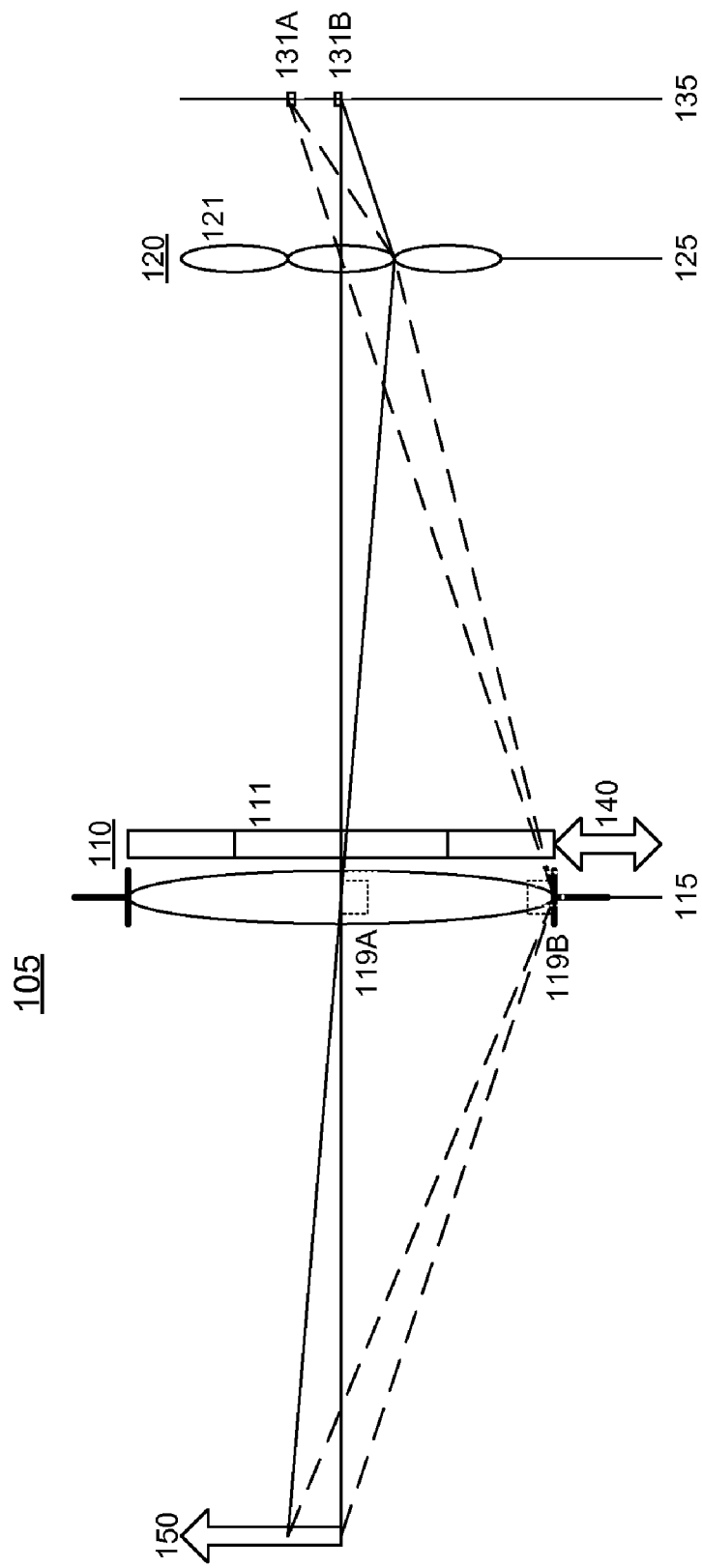
FIG. 1B illustrates the projection of a detector onto the aperture plane.
Figure 1C:
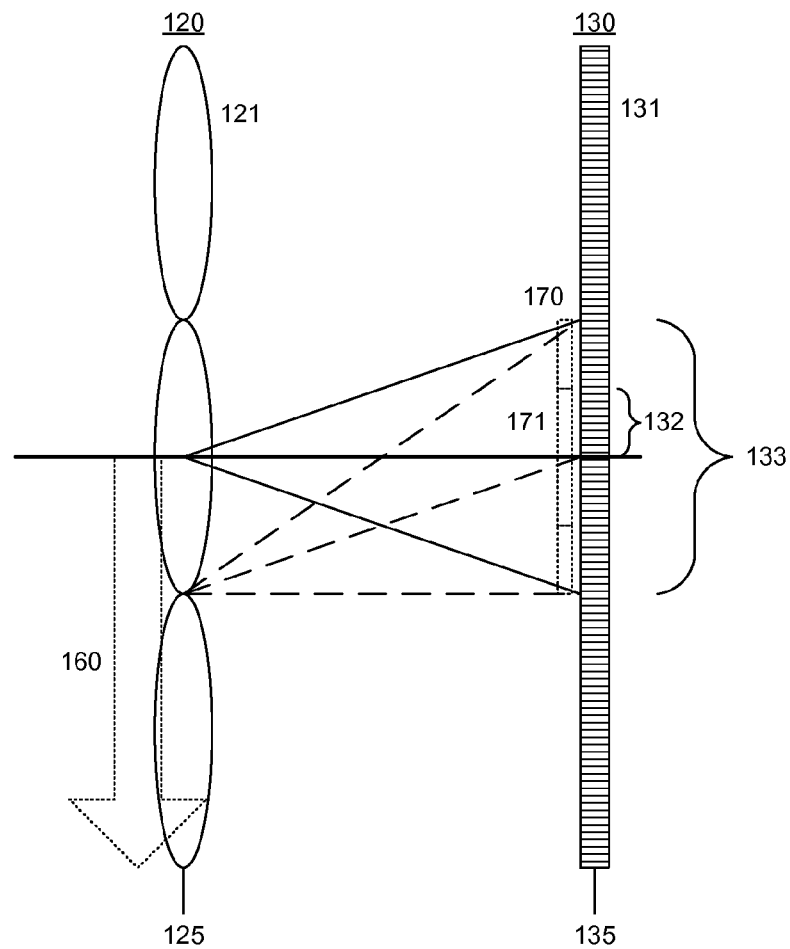
FIG. 1C is a detail of FIG. 1A.

FIGS. 1A-1C are diagrams of an adjustable multimode lightfield imaging system according to the invention. The system captures a multimode image of an object 150. The multimode lightfield imaging system includes an image-forming optical module 105, which in FIG. 1 is represented by a single lens element although it is understood that the optical module 105 could contain multiple elements and/or non-lens elements (e.g., mirrors). The optical module 105 forms an optical image 160 of object 150. The optical image 160 is formed at an image plane 125 of the optical module 105. The optical module 105 has an aperture 117 and aperture plane 115, which in FIG. 1 is represented by an aperture stop co-located with the single lens element. In more complex optical modules 105, the aperture 117 and aperture plane 115 need not be co-located with any of the optical elements within the optical module.

In a conventional imaging system, a detector array would be located at image plane 125 to capture the optical image 160. In a conventional color imaging system, an array of micro-filters (e.g., arranged in an R-G-B Bayer pattern) would be attached to the detector array at the image plane 125, so that each individual detector would capture red, green or blue channels of data.

However, this is not the case in FIG. 1. First, a non-homogeneous filter module 110 is positioned at the aperture plane 115. The filter module is non-homogeneous in that its filtering characteristics change as a function of location. In the following example, the filter module 110 is a filter array that includes different filters 111. For example, the filters 111 may have different wavelength responses, different polarization responses, or different luminance responses. However, the filter module is not required to be a filter array. It could be a filter with a continuously varying response, for example. A filter array is used in this example for purposes of illustration.

Typically, the filter module will be larger than the aperture 117 so that only a portion of the filter module will be illuminated.

Second, an array 120 of micro-imaging elements 121 is located at the image plane 125. In FIG. 1, the micro-imaging elements 121 are shown as microlenses. Other elements can also be used, for example, an array of pinholes. The detector array 130 is located behind (i.e., optically downstream of) the array 120 of micro-imaging elements. More specifically, the detector array 130 is positioned in a conjugate plane 135 to the aperture plane 115. That is, each micro-imaging element 121 directs light from the aperture plane 115 to the detector array 130 in the conjugate plane 135.

In the case of microlenses, each microlens 121 forms an image 170 of the aperture (and filter module) at the conjugate plane 135. The corresponding section of the detector array 130 may contain a single detector 131 or multiple detectors 131 (preferably, multiple detectors), and will be referred to as a "subarray" 133. Thus, in the example of FIG. 1, the detector array 130 is subdivided into subarrays 133, and each microlens 121 images the aperture and filter module onto a corresponding subarray 133. Each subarray 133 contains one or more detectors 131.

Conversely, referring to FIG. 1B, each individual detector 131 can be projected through a microlens 121 to a corresponding location 119 in the aperture plane 115 and on the filter module 110. For that specific detector 131, the microlens 121 collects light from the corresponding location 119. FIG. 1B shows the projection of detector 131A through the center microlens to location 119A, and the projection of detector 131B to location 119B. The projection 119 of the detector preferably is magnified by at least 10× relative to the actual detector size 131.

Referring to FIG. 1C for more detail, each microlens 121 images the entire filter array 110 (that falls within the aperture) onto a subarray 133. Each filter 111 covers only a portion of the filter array 110, so the image 171 of each filter 111 will cover only a portion of the subarray 133. That portion will be referred to as a subpixel 132, as shown in the detail of FIG. 1C. That is, each microlens 121 directs light from a filter 111 to a corresponding subpixel 132. Each subpixel 132 may contain one or more detectors but preferably contains one detector 131.

Each detector 131 collects the light from one filter 111 that travels through one microlens 121. The microlens array 120 is located in a conjugate plane to the object 150, so there is also an imaging relationship between the object 150 and the microlens array 120. Therefore, the light incident on a microlens is light originating from a portion of the object, not from the entire object. Thus, each detector 131 collects the light from a corresponding portion of the object (as determined by the extent of the microlens), as filtered by a corresponding filter 111.

Figure 2A:
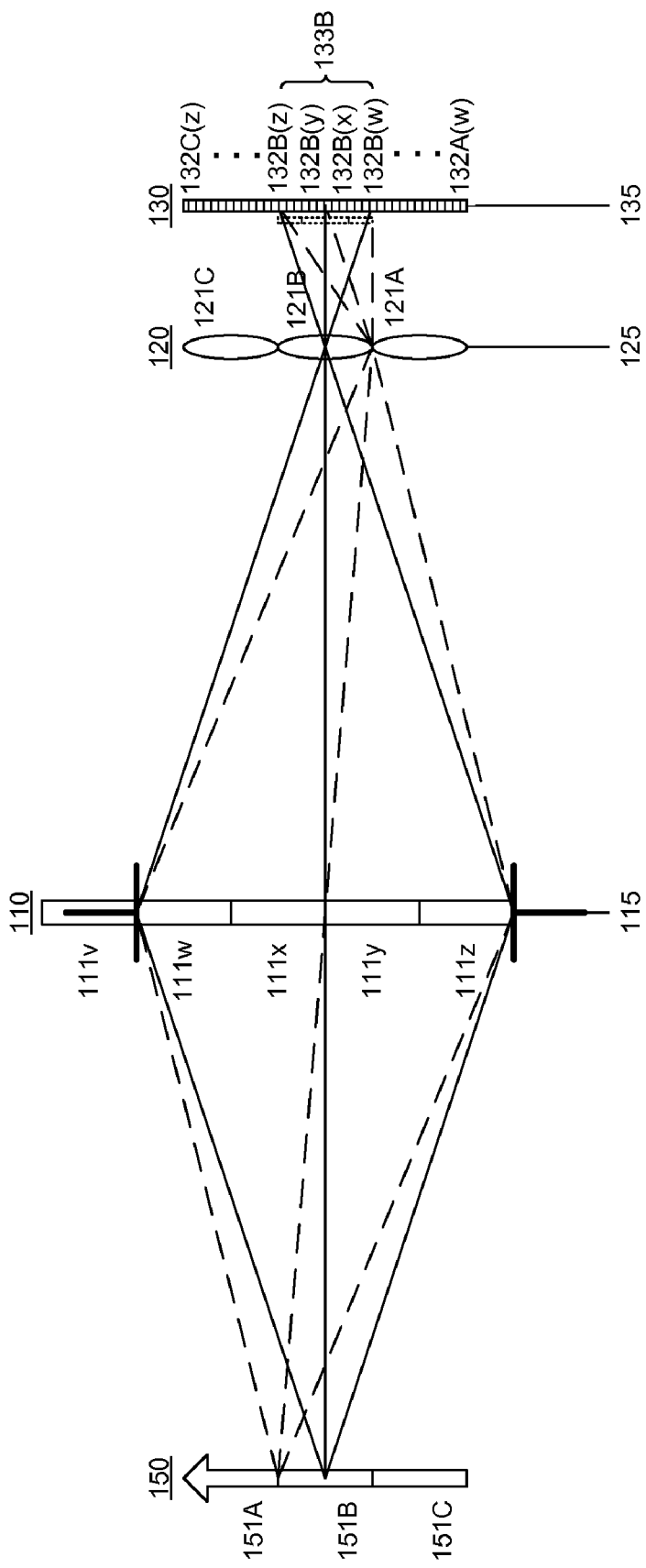
FIGS. 2A and 2B are diagrams further illustrating the operation of the system of FIG. 1.

FIG. 2A illustrates this concept in more detail. For clarity, the main lens 105 is omitted. In this example, the object 150 is divided into three subobjects 151A,B,C. Similarly, the illuminated portion of the filter array 110 includes four filters 111w,x,y,z. The filter module 110 is larger, also containing filter 111v which is not illuminated in FIG. 2A. The object 150 is imaged onto the microlens array 120. More specifically, the subobject 151B is imaged onto microlens 121B. This means that every ray that leaves subobject 151B will travel through the aperture (and through different filters 111, depending on where in the aperture) and arrive at microlens 121B. Similarly, subobject 151A is imaged onto microlens 121A, and subobject 151C is imaged onto microlens 121C.

Analogously, microlens 121B will image the entire filter array 110 (at least the illuminated portion) onto subarray 133B. Thus, filter 111w will be imaged by microlens 121B onto subpixel 132B(w), filter 111x onto subpixel 132B(x), and so on for the other filter/subpixel pairs, and for the other microlenses 121. For detectors 131 that fall entirely within subpixel 132B(w), those detectors will detect the light coming from subobject 151B passing through filter 111w. The same is true for the other subpixels 132A(w)-132C(z).

The imaging system is a "lightfield" imaging system because the rays collected by a detector are a function of not only the position in the object plane (as is the case in conventional imaging systems), but also a function of the position in the aperture plane. The imaging system is a multimode imaging system because the filter module 110 captures multimode information.

Referring again to FIG. 1, a digital processing unit 180 collects the data from the detector array 130 and processes it accordingly. As a simple example, the digital processing unit 180 may reorder the data, collecting together the data from subpixels 132A(w), 132B(w) and 132C(w) in order to form an image as filtered by filter 111w. The same can be done for filters 111x,y,z.

Figure 2B:
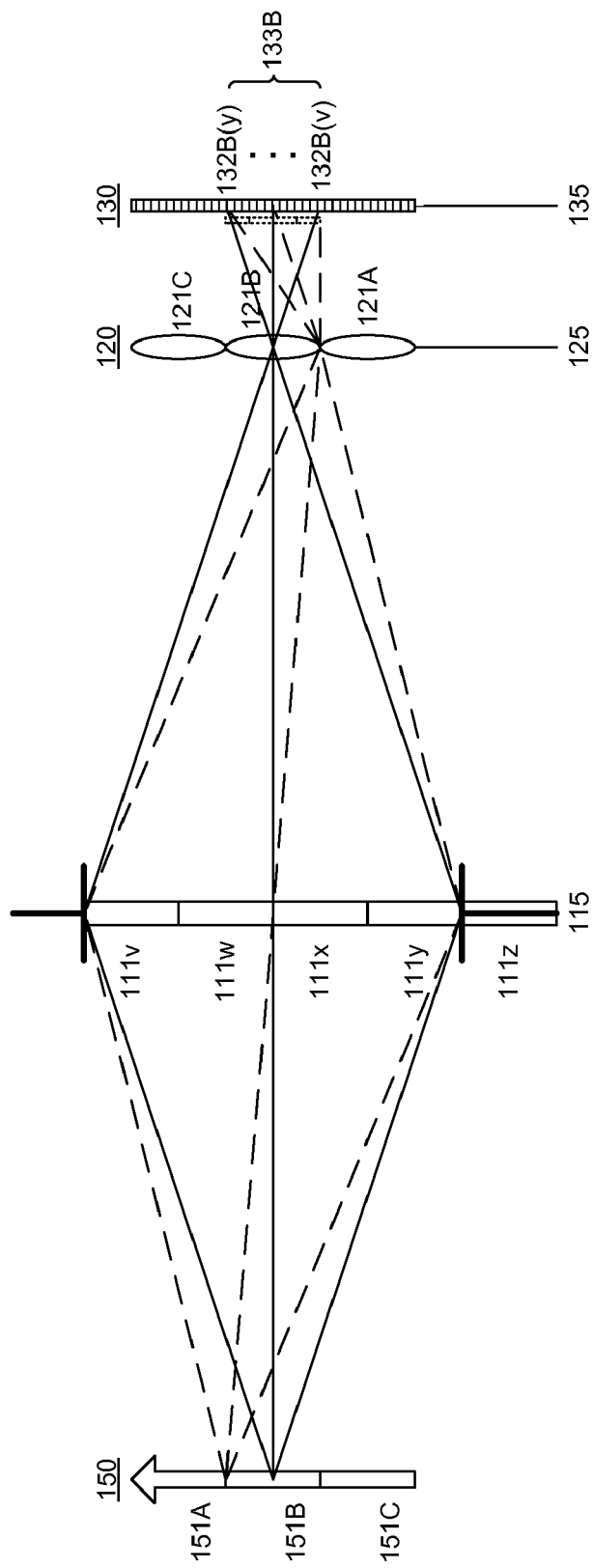

The system also includes an actuator 140 that can change the position of the filter module 110 relative to the optical module 105. In this way, which filters 111 are directed to which subpixels 132 can be changed, thereby changing the effective filtering. For example, in FIG. 2B, the filter array 110 has been translated downward so that filters 111v,w,x,y are now illuminated.

Figure 3:
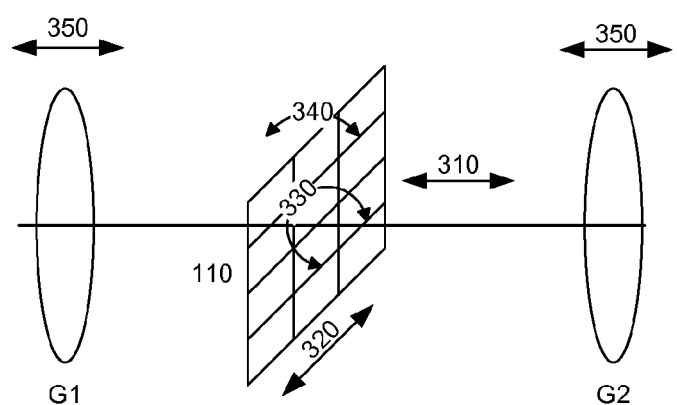
FIG. 3 is a diagram showing different types of relative movement between the filter module and the optical module.

Different types of movement can be used to change the filtering. FIG. 3 is a diagram showing different types of relative movement between the filter module 110 and the optical module. In this example, the optical module contains two lens groups G1 and G2, with the aperture plane and filter module 110 located between the two lens groups. As one example, the actuator 140 might translate the filter module 110 relative to the optical module 105, along a direction 310 parallel to an optical axis, along a direction 320 that lies in the aperture plane, or along other directions. Alternately, the actuator 140 might rotate 330 the filter module 110 within the aperture plane. As another example, the actuator 140 might tilt 340 the filter module 110 relative to the optical module 105. Note that the actuator may move the optical module (or optical elements within the optical module) rather than moving the filter module, so long as there is relative motion between the filter module and the optical module. Movement 350 shows movement of optical elements within the optical module, for example a zoom action.

FIGS. 4-7 show some additional examples.

Figure 4A:
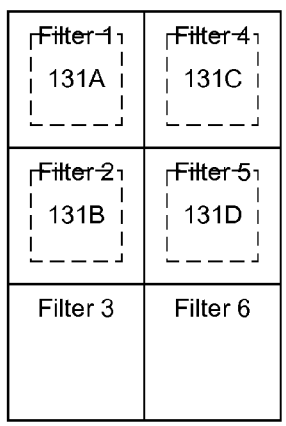
FIGS. 4A-4C show an example based on a filter array translated in the aperture plane.
Figure 4B:
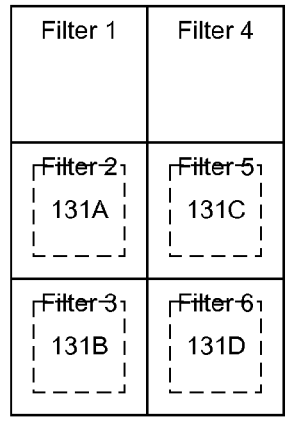
Figure 4C:
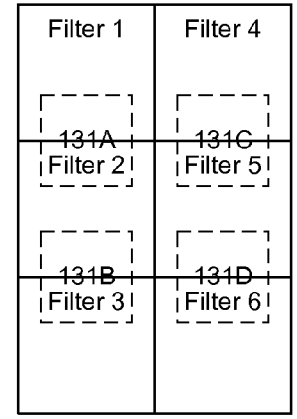

FIGS. 4A-4C show the illumination of a filter array 110, when it is translated along a direction that lies in the aperture plane. In this example, the filter array contains four filters 1-6, as indicated by the solid outlines. The projection of the detectors from one subarray (i.e., the detectors corresponding to one microlens) are shown superimposed in dashed outlines lines. In this example, there are four detectors 131A-D. Each of FIGS. 4A-C corresponds to the filter array in a different position. In the position of FIG. 4A, light illuminates filters 1,2,4,5 of the array. The light passing through filter 1 is collected onto detector 131A, so that signal corresponds to light filtered by filter 1. Similarly, detector 131B collects light passing through filter 2, detector 131C collects light passing through filter 4 and detector 131D collects light passing through filter 5. All of this light originates from the same subobject since it is all passing through the same microlens. Thus, detectors 131A-D capture spectral (or other multimode) information about one subobject region of the overall object.

In FIG. 4B, the filter array has been moved. In this position, light illuminates filters 2,3,5,6 of the array. Detector 131A collects light passing through filter 2, detector 131B collects light passing through filter 3, detector 131C collects light passing through filter 5 and detector 131D collects light passing through filter 6.

In many cases, the system will be designed so that each detector collects the light passing through only one filter. However, this is not required. In the position of FIG. 4C, detector 131A "experiences" 50% filter 1 and 50% filter 2, detector 131B experiences 50% filter 2 and 50% filter 3, and so on. FIG. 4 is just an example. The filter array may have alternate geometric layouts and shapes as well as different combinations of filters in order to implement various multimode imaging.

This architecture has several advantages over a conventional approach. A conventional approach might use two filter wheels, one containing filters 1,2,4,5 when that spectral analysis is desired and another containing filters 2,3,5,6 for the alternate spectral analysis. When the 1,2,4,5 filter wheel is used, each of the filters 1,2,4,5 rotates through the illumination path in sequence. This results in time multiplexing of the spectral information (rather than single snapshot capture of the spectral information). Furthermore, if the 2,3,5,6 analysis is desired, the filter wheel must be changed, rather than simply shifting the filter module as in FIG. 4.

Figure 5A:
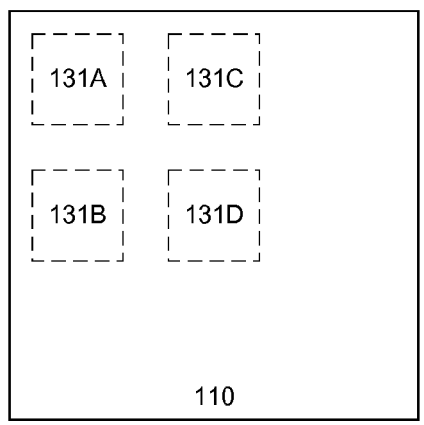
FIGS. 5A-5B show another example based on a non-arrayed filter module translated in the aperture plane.
Figure 5B:
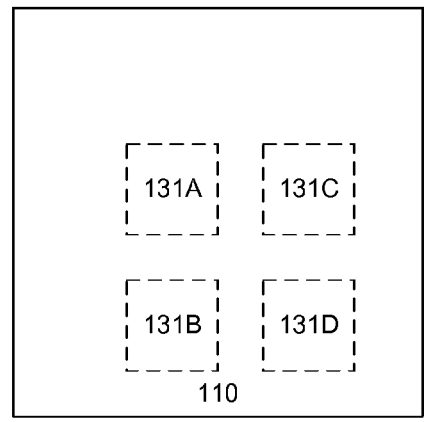

FIGS. 5A-5B show an example where the filter module is not an array, but is a continuously varying non-homogeneous filter. In this example, the filter module 110 varies in both x and y. For example, the filter module might be a wavelength filter that has a different center wavelength along the x direction and a different filter bandwidth along the y direction. When the filter module is moved from position 5A to 5B, each detector 131 will capture different information depending on which part of the filter module corresponds to that detector.

As another example, the filter module in FIG. 5 might have a wavelength response that varies as a function of x and a polarization response that varies as a function of y. Furthermore, this might be implemented as two filters, a wavelength filter and a polarization filter, which are moved independently of each other.

Figure 6A:
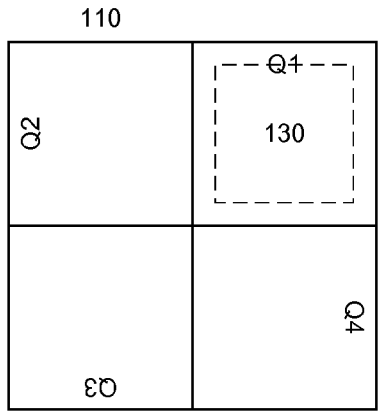
FIGS. 6A-6B show an example based on a filter array rotated in the aperture plane.
Figure 6B:
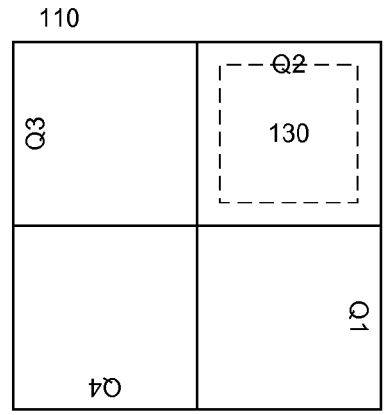

FIGS. 6A-6B show an example based on a filter module rotated in the aperture plane. In this example, the filter module has four quadrants Q1-Q4 that have different filter responses. Dashed outline 130 is the outline of the detector array projected onto the aperture plane. In FIG. 6A, quadrant 1 is illuminated. In FIG. 6B, the filter module is rotated clockwise by ninety degrees and quadrant 2 is illuminated, resulting in a different filtering.

Figure 7A:
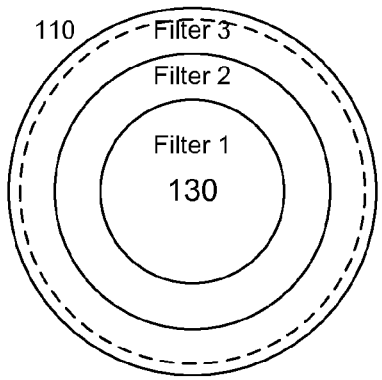
FIGS. 7A-7B show an example based on movement along the optical axis.
Figure 7B:
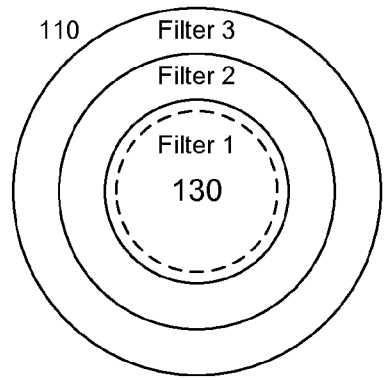

FIGS. 7A-7B show an example based on movement along the optical axis. In this example, the filter module is a set of concentric filters 1-3. In the position of FIG. 7A, all three filters are illuminated (as indicated by the dashed circle). In FIG. 7B, only the center filter 1 is illuminated. This might be achieved with a zoom lens, for example. Referring to FIG. 3, both lens groups G1 and G2 might move along the optical axis. If the filter module is positioned between the two lens groups, then zooming the lenses can change the footprint of the optical beam on the filter module, with the consequence that light passes only through a larger or smaller portion of the filter module. If the filter module is segmented as in FIG. 7, in the zoom-in configuration only a few filters in the inner rings might be used effectively, whereas in the zoom-out configuration the filters of the outer rings might also be used.

This approach might be used in an application where spatial and spectral resolution are traded off. Detailed images of the object (i.e., high spatial resolution) may be formed when zoomed in, but with lower spectral resolution or less spectral information. When zoomed out, increased spectral resolution may be achieved at the expense of spatial resolution.

Other types of movement can also be used to change which filters are illuminated.

As a final example, consider a multispectral imaging task that involves detecting different types of spectral signals. For example, the classification of plant matter as either dry or fresh requires different spectral signatures for different crop types such as rice, corn, wheat. Preferably, a single, multi-spectral imaging system could be adjusted to address the different crop types, rather than requiring a separate filter wheel for each crop type.

Figure 8A:
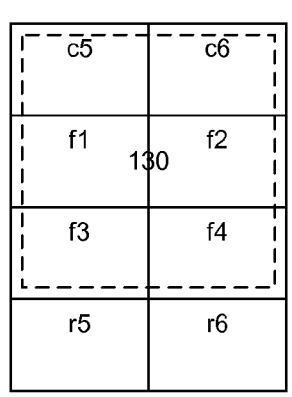
FIGS. 8A-8B show an example for distinguishing between dry and fresh vegetation, for both corn and rice.
Figure 8B:
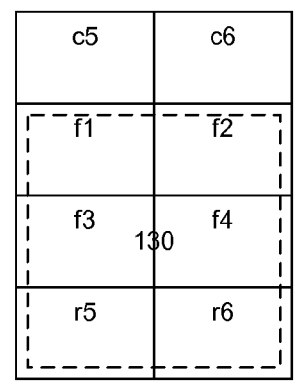

FIGS. 8A-8B show an example filter array for differentiating between dry and fresh vegetation using a simple shift of the filter module in the aperture plane. The filters f1-f4 and c5, c6, r5, r6 are specified in Tables 1-3.

TABLE 1

Filter specifications for common filters used to detect fresh/dry rice/corn leaf

| index | filter (Long/Short) | Cut off (nm) | transmittance (%) |
|---|---|---|---|
| f1 | L | 450 | 0.55 |
| f2 | L | 500 | 0.55 |
| f3 | L | 550 | 0.55 |
| f4 | S | 950 | 0.55 |

TABLE 2

Filters specifications for corn-specific filters

| index | center wavelength (nm) | bandwidth (nm) | transmittance (%) |
|---|---|---|---|
| c5 | 900 | 70 | 0.6 |
| c6 | 950 | 40 | 0.45 |

TABLE 3

Filter specifications for rice-specific filters

| index | center wavelength (nm) | bandwidth (nm) | transmittance (%) |
|---|---|---|---|
| r5 | 600 | 80 | 0.6 |
| r6 | 650 | 70 | 0.6 |

Filters f1-f4 and c5,c6 are used to identify corn, and to distinguish between fresh and dry corn leaf. Filters f1-f4 and r5,r6 are used to identify rice, and to distinguish between fresh and dry rice leaf. Note that filters f1-f4 are shared filters that are common to both corn and rice. The filter specifications in Tables 1-3 were chosen from a dictionary of commercially available filters.

When detecting corn, the filter array is positioned as shown in FIG. 8A relative to the detector array 130, thus illuminating filters f1-f4 and c5,c6. When detecting rice, the filter array is positioned as shown in FIG. 8B, using filters f1-f4 and r5,r6. Thus a single system can be used for both corn and rice.

Although the detailed description contains many specifics, these should not be construed as limiting the scope of the invention but merely as illustrating different examples and aspects of the invention. It should be appreciated that the scope of the invention includes other embodiments not discussed in detail above.

For example, many types of filter arrays can be implemented. Filters can have different wavelength responses. All of the filters can be different, or some can be different and some the same. Multiple filters or filter arrays can also be used. For example, multiple filter arrays or filter modules can be used, each of which is moved independently of the others (or not). The number and type of wavelength responses can also vary, depending on the application. Some applications will use many different wavelength filters: 10, 20, 25 or more. In some cases, specific wavelength lines are being detected, so narrow band interference filters may be used. Filters other than wavelength filters can also be used, for example polarization, luminance, and neutral density filters.

Filtering can also be implemented at other points in the system. For example, the invention does not prevent the use of traditional micro-filters with the detector array. Various types of optical modules can also be used, including reflective and catadioptric systems. In some applications, the optical module is preferably telecentric. Finally, terms such as "light" and "optical" are not meant to be limited to the visible or purely optical regions of the electromagnetic spectrum, but are meant to also include regions such as the ultraviolet and infrared (but not be limited to these).

Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents.

What is claimed is:

1. An adjustable multimode lightfield imaging system comprising:
    an image-forming optical module that forms an optical image of an object, the optical image formed at an image plane, the image-forming optical module having an aperture plane;
    a non-homogeneous filter module positioned approximately at the aperture plane, a portion of the filter module illuminated by the object;
    an array of micro-imaging elements positioned at the image plane;
    a detector array positioned in a conjugate plane to the aperture plane, the micro-imaging elements imaging the illuminated portion of the filter module onto the detector array, the detectors receiving light collected by the micro-imaging elements from corresponding locations of the filter module; and
    an actuator coupled to change a position of the filter module relative to the image-forming optical module, whereby the detectors receive light collected by the micro-imaging elements from different locations of the filter module.

2. The lightfield imaging system of claim 1 wherein:
    the non-homogeneous filter module comprises a filter array, the filter array including filters with at least two different responses;
    the detector array is subdivided into subarrays of detectors;
    the micro-imaging elements image illuminated filters onto corresponding subarrays; and
    changing the position of the filter module relative to the optical module, changes which filters are imaged onto which subarrays.

3. The lightfield imaging system of claim 2 wherein the actuator translates the filter module relative to the image-forming optical module, along a direction parallel to an optical axis of the image-forming optical module.

4. The lightfield imaging system of claim 2 wherein the actuator translates the filter module relative to the image-forming optical module, along a direction in the aperture plane.

5. The lightfield imaging system of claim 2 wherein the actuator rotates the filter module within the aperture plane relative to the image-forming optical module.

6. The lightfield imaging system of claim 2 wherein the filter array includes filters with at least 10 different wavelength responses.

7. The lightfield imaging system of claim 2 wherein the filter array includes narrow band interference filters with different wavelength responses.

8. The lightfield imaging system of claim 2 wherein the filter array includes narrow band interference filters and wide band wavelength filters with different wavelength responses.

9. The lightfield imaging system of claim 2 wherein the filter array implements multispectral imaging.

10. The lightfield imaging system of claim 2 wherein the filter array includes filters with different polarization responses.

11. The lightfield imaging system of claim 2 wherein the filter array includes different luminance filters.

12. The lightfield imaging system of claim 2 wherein the filter array includes different neutral density filters.

13. The lightfield imaging system of claim 2 wherein the filter module in a first position illuminates filters to analyze a first substance, and the filter module in a second position illuminates filters to analyze a second substance.

14. The lightfield imaging system of claim 13 wherein a majority of the filters that are illuminated in the first position are also illuminated in the second position.

15. The lightfield imaging system of claim 2 wherein the filter array analyzes multiple substances, the filters in a central region of the filter array are common to analyzing all substances, and the filters around a periphery of the filter array are specific to individual substances.

16. The lightfield imaging system of claim 1 wherein the array of micro-imaging elements includes a microlens array.

17. The lightfield imaging system of claim 1 wherein the array of micro-imaging elements includes an array of pinholes.

18. The lightfield imaging system of claim 1 wherein the image-forming optical module is telecentric.

19. The lightfield imaging system of claim 1 wherein the aperture plane has a magnification of at least 10:1 relative to the detector array.

20. The lightfield imaging system of claim 1 further comprising:
 a micro-filter array positioned over the detector array, light directed to each detector being filtered by a micro-filter in the micro-filter array.

* * * * *